(12) United States Patent
Taniguchi et al.

(10) Patent No.: US 11,511,064 B2
(45) Date of Patent: Nov. 29, 2022

(54) INTUBATION APPARATUS

(71) Applicant: NIHON KOHDEN CORPORATION, Tokyo (JP)

(72) Inventors: Yukio Taniguchi, Tokorozawa (JP); Tsutomu Wakabayashi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 829 days.

(21) Appl. No.: 16/365,911

(22) Filed: Mar. 27, 2019

(65) Prior Publication Data

US 2019/0298951 A1    Oct. 3, 2019

(30) Foreign Application Priority Data

Mar. 28, 2018    (JP) .............................. JP2018-062119

(51) Int. Cl.
*A61B 1/267*    (2006.01)
*A61B 1/04*    (2006.01)
(Continued)

(52) U.S. Cl.
CPC ..... *A61M 16/0488* (2013.01); *A61B 1/00052* (2013.01); *A61B 1/04* (2013.01); *A61B 1/267* (2013.01)

(58) Field of Classification Search
CPC ........ A61M 16/0488; A61M 2205/502; A61M 2205/582; A61M 2205/584;
(Continued)

(56) References Cited

U.S. PATENT DOCUMENTS

2007/0106122 A1    5/2007    Yokota et al.
2011/0263935 A1    10/2011    Qiu
(Continued)

FOREIGN PATENT DOCUMENTS

JP    2004-089484 A    3/2004
JP    2007-144123 A    6/2007
(Continued)

OTHER PUBLICATIONS

Japanese Office Action dated Oct. 5, 2021 issued in Japanese Patent Application No. 2018-062119.

*Primary Examiner* — Aaron B Fairchild
(74) *Attorney, Agent, or Firm* — Pearne & Gordon LLP

(57) ABSTRACT

An intubation apparatus includes an inserting section that has an elongated shape and is to be inserted from a mouth of a subject toward a target site. An intubation tube is formed to extend along a longitudinal direction of the inserting section and is advanceable and retractable with respect to the inserting section. An imaging section is placed at a tip end of the inserting section and takes an in vivo image of the body of the subject. A detecting section detects a target site from the in vivo image based on a feature amount of the target site that is preset. A notifying section is disposed integrally with or separately from the intubation apparatus and notifies an operator who operates the inserting section. A notification controller controls the notifying section to notify of information relating to the target site of the subject based on a result of the detection.

13 Claims, 7 Drawing Sheets

(51) Int. Cl.
*A61B 1/00* (2006.01)
*A61M 16/04* (2006.01)

(58) Field of Classification Search
CPC ...... A61M 2205/583; A61M 2205/581; A61B
1/00052; A61B 1/04; A61B 1/267; A61B
1/0005; A61B 1/00009; A61B 2034/2065;
A61B 1/000094; A61B 1/043
See application file for complete search history.

(56) References Cited

U.S. PATENT DOCUMENTS

| | | | |
|---|---|---|---|
| 2013/0229503 A1* | 9/2013 | Taniguchi | A61B 1/000094 |
| | | | 348/65 |
| 2016/0022943 A1 | 1/2016 | Kanowitz | |
| 2016/0148053 A1* | 5/2016 | Matsuzaki | G06T 7/246 |
| | | | 382/128 |
| 2017/0291001 A1* | 10/2017 | Rosenblatt | A61B 5/743 |
| 2017/0337683 A1* | 11/2017 | Yoshida | A61B 10/06 |
| 2018/0129914 A1* | 5/2018 | Kariya | G06V 20/00 |
| 2018/0193102 A1* | 7/2018 | Inoue | A61B 1/05 |
| 2018/0307933 A1* | 10/2018 | Iwaki | G06T 11/60 |

FOREIGN PATENT DOCUMENTS

| | | |
|---|---|---|
| JP | 2013-085880 A | 5/2013 |
| WO | 2017/151796 A1 | 9/2017 |

\* cited by examiner

INTUBATION APPARATUS

CROSS REFERENCE TO RELATED APPLICATION

This application is based on Japanese Patent Application No. 2018-062119 filed on Mar. 28, 2018, the contents of which are incorporated herein by reference.

BACKGROUND

The present invention relates to an intubation apparatus, and particularly to an intubation apparatus which inserts an intubation tube into a target site along an inserting section that is inserted through the mouth of a subject.

In an intubation into a target site such as the trachea, conventionally, an intubation tube is inserted toward the target site while spreading the larynx with a laryngoscope which is inserted through the mouth of the subject, and directly viewing the target site from the outside. However, it is difficult to clearly view the target site and a tip end portion of the intubation tube from the outside, and there is a possibility that the intubation tube may not be smoothly inserted into the target site.

As a technique for enabling a target site and a tip end portion of an intubation tube to be clearly viewed, for example, JP-A-2007-144123 proposes an intubation support apparatus which exhibits operability in the case where an insertion tool is inserted into the trachea of a patient.

When the intubation support apparatus is used, an image of an observation site where the tip end of the insertion tool exists is taken by imaging means, and the taken image is displayed on a displaying section. Therefore, the trachea and the tip end portion of the intubation tube can be clearly seen through the image.

In the intubation support apparatus of JP-A-2007-144123, however, there is a possibility that an intubation into the trachea requires a considerably longer time period in the case where, for example, the operator cannot easily recognize the trachea from an image which is displayed on a displaying section. When vomitus, blood, or the like makes the image unclear, for example, it is difficult to quickly distinguish between the trachea and the esophagus. Particularly, there is a possibility that an unskilled person who is less-experienced in intubation requires a long time period to recognize the trachea.

The invention has been conducted in order to solve the problem in the prior art. It is an object of the invention to provide an intubation apparatus in which intubation to the target site is quickly performed.

SUMMARY OF THE INVENTION

The intubation apparatus of the presently disclosed subject matter includes: an inserting section which has an elongated shape, and which is to be inserted from a mouth of a subject toward a target site; an intubation tube which is formed to extend along a longitudinal direction of the inserting section, and which is disposed so as to be advanceable and retractable with respect to the inserting section; and an imaging section which is placed in a vicinity of a tip end portion of the inserting section, and which takes an image of an interior of the body of the subject, wherein the apparatus further includes: a detecting section which detects a target site from an in vivo image that is taken by the imaging section, based on a feature amount of the target site that is preset; a notifying section which is disposed integrally with and/or separately from the intubation apparatus, and which notifies an operator who operates the inserting section, of information; and a notification controller which controls the notifying section so as to notify of information relating to the target site of the subject, based on a result of the detection of the detecting section.

Here, preferably, the information relating to the target site of the subject may be supporting information for supporting an operation of the inserting section.

Preferably, the notifying section may have a displaying section which displays the in vivo image that is taken by the imaging section, and the notification controller may change a display state of the displaying section so as to notify of supporting information for supporting an operation of the inserting section, based on the result of the detection of the detecting section.

In a case where the target site is detected by the detecting section, preferably, the notification controller may cause a site mark to be displayed at a position of the target site while being superimposed on the in vivo image, thereby notifying of the supporting information.

Based on a feature amount of a non-target site which is different from the target site, the detecting section may detect the non-target site from the in vivo image based on a feature amount of the non-target site, and, in a case where the non-target site is detected by the detecting section, the notification controller may cause a non-site mark which is different from the site mark, to be displayed at a position of the non-target site while being superimposed on the in vivo image, thereby notifying of the supporting information.

Preferably, the apparatus may further have an intubation determining section which determines whether an intubation tube is insertable into the target site or not, based on a position of the target site which is detected by the detecting section, and an advancing direction of the intubation tube, and the notification controller may change a display state of the displaying section, based on the result of the determination of the intubation determining section, thereby notifying of the supporting information.

If the intubation determining section determines that the intubation tube is insertable into the target site, the notification controller may change a display state of the site mark which is displayed at the position of the target site that is detected by the detecting section, while being superimposed on the in vivo image, thereby notifying of the supporting information.

The detecting section may detect the non-target site which is different from the target site, from the in vivo image based on a feature amount of the non-target site, the intubation determining section may determine whether the intubation tube is insertable into the non-target site or not, based on a position of the non-target site which is detected by the detecting section, and the advancing direction of the intubation tube, and, if the intubation determining section determines that the intubation tube is insertable into the non-target site, the notification controller may erase a target mark which is displayed on the displaying section in order to indicate the advancing direction of the intubation tube, thereby notifying of the supporting information.

The notifying section may further have at least one of a vibrating section which vibrates a grasping portion that is to be grasped by an operator, and a sound outputting section that outputs a warning sound to the operator, and, if the intubation determining section determines that the intubation tube is insertable into the non-target site, the notification controller may cause at least one of the vibrating section and the sound outputting section to operate, thereby notifying of the supporting information.

The displaying section may display the target mark indicating the advancing direction of the intubation tube, while being superimposed on the in vivo image, the target mark may have a shape which indicates an outer diameter of the intubation tube, and a size of the target site with respect to the shape may be changed in accordance with an insertion distance by which the inserting section is inserted into a body, thereby notifying of supporting information for supporting the operation of the inserting section.

The detecting section may detect a glottis as the target site.

According to the presently disclosed subject matter, the detecting section detects the target site from the in vivo image which is taken by the imaging section, based on the feature amount of the target site that is preset, the notification controller controls the notifying section so as to notify of information relating to the target site of the subject, based on a result of the detection of the detecting section, and therefore it is possible to provide an intubation apparatus in which intubation to the target site is quickly performed.

DETAILED DESCRIPTION OF EMBODIMENTS

Hereinafter, embodiments of the presently disclosed subject matter will be described with reference to the accompanying drawings.

Embodiment 1

Figure 1A:
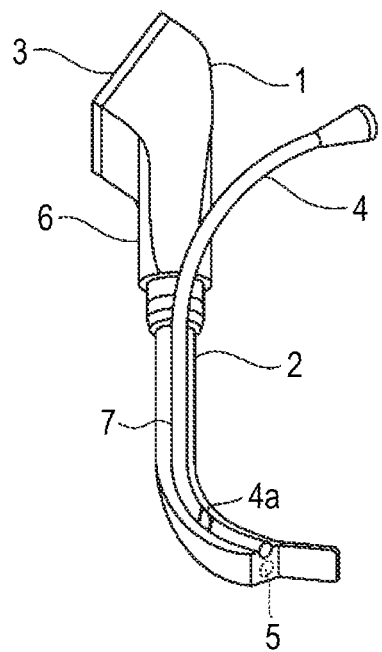
FIGS. 1A and 1B are views illustrating the configuration of an intubation apparatus of Embodiment 1 of the presently disclosed subject matter.
Figure 1B:
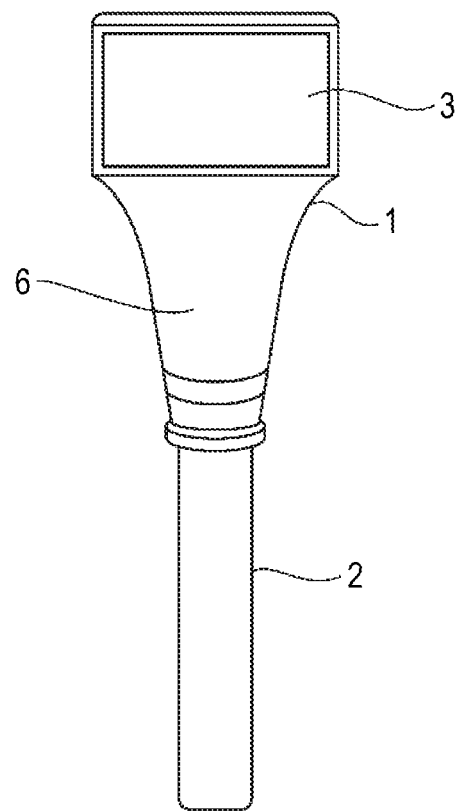

FIGS. 1A and 1B illustrate the configuration of an intubation apparatus of Embodiment 1 of the presently disclosed subject matter. The intubation apparatus may include an apparatus body 1, an inserting section 2 is detachably attached to a lower portion of the apparatus body 1, and a displaying section 3 is disposed in an upper portion of the apparatus body 1. An intubation tube 4 is placed along a side portion of the inserting section 2, and an imaging section 5 is placed in the vicinity of a tip end portion of the inserting section 2. In FIG. 1B, the intubation tube 4 is not illustrated.

The operator operates the apparatus body 1 to perform intubation. A grasping portion 6 is formed in the lower half portion of the apparatus body. In order to allow the operator to easily grasp the grasping portion 6, the grasping portion has a size which enables the portion to fit in the hand of the operator, and is formed into a columnar shape.

The inserting section 2 is to be inserted from the mouth of the subject toward the glottis, has an elongated shape, and is formed so that the tip end side is arcuated. A groove portion 7 which elongates from the basal end portion to the tip end portion is formed in the side portion of the inserting section 2. The groove portion 7 holds the intubation tube 4 in an advanceable and retractable manner, and is formed so as to have a size which corresponds to the intubation tube 4.

The intubation tube 4 has a tubular shape, and is formed so as to elongate along the groove portion 7 of the inserting section 2. Here, the intubation tube 4 is placed in the groove portion 7 in a manner that the tube is advanceable into and retractable from the tip end portion of the inserting section 2, and can be advanced in a predetermined advancing direction while being restricted by the groove portion 7. An insertion mark 4a which functions as a guide in the case where the intubation tube 4 is to be inserted into the glottis is formed in the vicinity of the tip end portion of the intubation tube 4.

The imaging section 5 takes an in vivo image of the subject, and is placed so as to be forwardly directed in the vicinity of the tip end portion of the inserting section 2. Namely, the imaging section is placed so as to be directed in a direction along which an extension of the inserting section 2 extends. For example, the imaging section 5 may be configured by a CCD image sensor or the like.

The displaying section 3 is connected to the imaging section 5, and displays an in vivo image which is taken by the imaging section 5 in order to enable the operator to operate the inserting section 2 and the intubation tube 4. For example, the displaying section 3 may be configured by a display device such as a liquid crystal display.

Next, the configuration of the apparatus body 1 will be described in detail.

Figure 2:
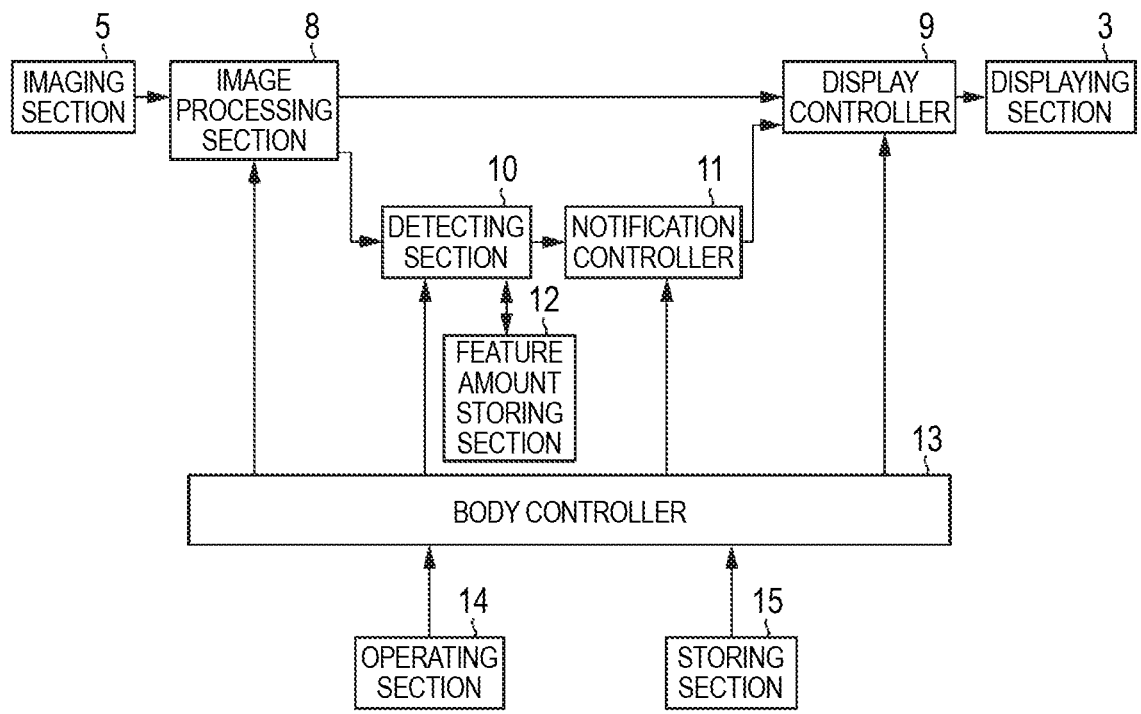
FIG. 2 is a block diagram illustrating the configuration of the apparatus body.

As illustrated in FIG. 2, the apparatus body 1 may include an image processing section 8 which is connected to the imaging section 5, and a display controller 9 and the displaying section 3 are sequentially connected to the image processing section 8. The image processing section 8 is sequentially connected to a detecting section 10 and a notification controller 11, and the notification controller 11 is connected to the display controller 9. A feature amount storing section 12 is connected to the detecting section 10. Furthermore, a body controller 13 is connected to the image processing section 8, the detecting section 10, the notification controller 11, and the display controller 9, and an operating section 14 and a storing section 15 are connected to the body controller 13.

The image processing section 8 processes an image signal of the in vivo image which is taken by the imaging section 5, and produces an in vivo image which is to be displayed on the displaying section 3.

The display controller 9 controls the displaying section 3 so as to display the in vivo image which is produced by the image processing section 8. The display controller 9 causes a target mark indicating a predetermined position in the advancing direction of the intubation tube 4, to be displayed on the displaying section 3 with superimposed on the in vivo image. Here, the advancing direction of the intubation tube 4 is previously set, based on the forming direction of the groove portion 7 in the inserting section 2. For example, the advancing direction is set on the extension of the groove portion 7.

The feature amount storing section 12 is configured by a memory, a hard disk drive, or the like, extracts the feature amount of an image of the glottis which is previously taken, and stores the feature amount. Examples of the feature amount of the glottis are the shape value of the vocal cords, the chromaticity of the vocal cords, and the like.

The detecting section 10 detects the glottis from the in vivo image which is produced by the image processing section 8, as the target site based on the feature amount of the glottis which is read from the feature amount storing section 12.

The notification controller 11 changes the display state of the displaying section 3 through the display controller 9 based on the result of the detection of the detecting section 10, thereby notifying of supporting information for supporting an operation of the inserting section 2 by the operator. In the case where the detecting section 10 detects the glottis, specifically, the notification controller 11 causes the site mark to be displayed at the position of the glottis with superimposed on the in vivo image, thereby notifying of supporting information.

Here, the displaying section 3 has a function of notifying of the supporting information in addition to that of displaying the in vivo image, and constitutes the notifying section in the presently disclosed subject matter.

The operating section 14 is used for enabling the operator to perform an input operation, and may be configured by buttons, a touch panel, and the like.

The storing section 15 stores an operation program and the like, and may be configured by a storage device such as a memory, a hard disk drive, or an SD card.

The body controller 13 controls the sections in the intubation apparatus based on various operation signals and the like which are input by the operator through the operating section 14.

The image processing section 8, the display controller 9, the detecting section 10, the notification controller 11, and the body controller 13 are configured by a CPU and operation programs which cause the CPU to perform various processes, or alternatively they may be configured by digital circuits.

Next, the operation of the embodiment will be described.

Figure 3:
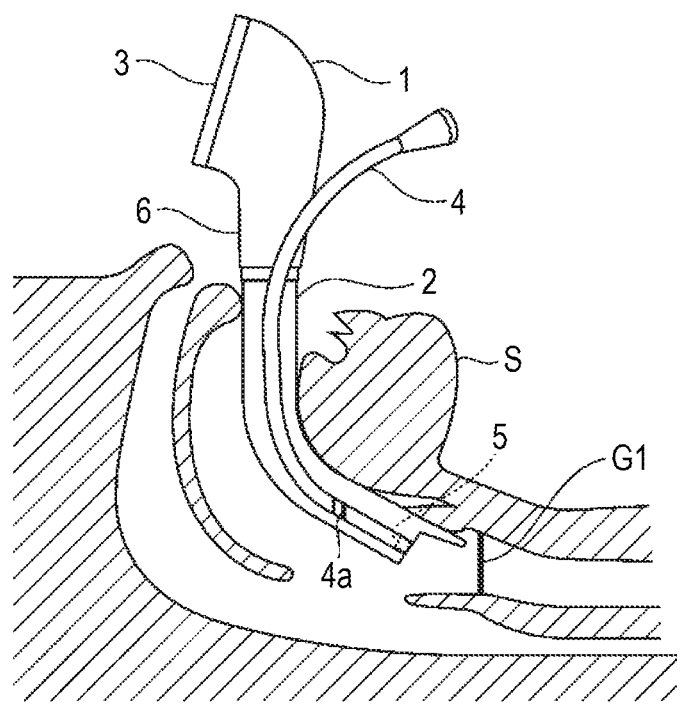
FIG. 3 is a view illustrating a manner of inserting an inserting section through the mouse of a subject.

In the intubation apparatus illustrated in FIG. 1, first, a power supplying section which is not illustrated is turned ON, and the sections of the intubation apparatus are activated. Then, the operator inserts the inserting section 2 through the mouth of the subject S toward the glottis G1 as illustrated in FIG. 3. At this time, an in vivo image of the subject S is taken by the imaging section 5 which is placed in the vicinity of the tip end portion of the inserting section 2, and image signals of the in vivo image are sequentially supplied from the imaging section 5 to the image processing section 8 as illustrated in FIG. 2. The image processing section 8 produces an in vivo image which is to be displayed on the displaying section 3, based on the image signals of the in vivo image, and supplies the produced in vivo image to the display controller 9 and the detecting section 10.

Figure 4:
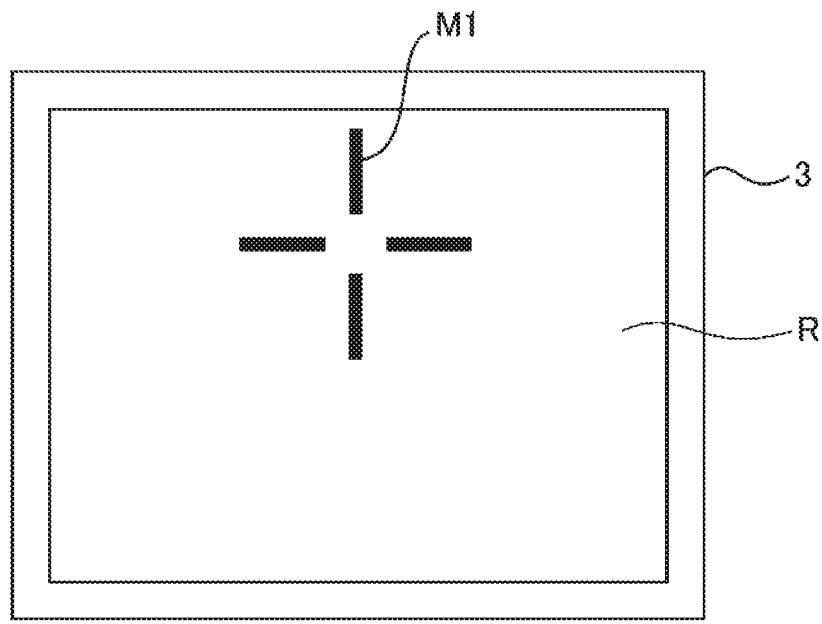
FIG. 4 is a view illustrating a manner of displaying a target mark while being superimposed on an in vivo image.

When the in vivo image which is produced by the image processing section 8 is supplied to the display controller 9, the display controller 9 causes the in vivo image to be displayed on the displaying section 3. Therefore, the operator can safely insert the inserting section 2 toward the glottis G1 while visually recognizing the in vivo image which is displayed on the displaying section 3. At this time, as illustrated in FIG. 4, the display controller 9 causes a target mark M1 to be displayed on the displaying section 3 with superimposed on the composite image R at a position corresponding to the preset advancing direction of the intubation tube 4. For example, the target mark M1 may be displayed in green.

When the in vivo image which is produced by the image processing section 8 is supplied to the detecting section 10, the detecting section 10 detects the glottis G1 contained in the in vivo image based on the feature amount of a glottis. Specifically, the detecting section 10 searches the glottis G1 contained in the in vivo image R based on the feature amount of a glottis G2 which is stored in the feature amount storing section 12. Examples of the feature amount of the glottis G2 are the shape value of the vocal cords constituting the glottis G1, the chromaticity of the vocal cords, and the like. Usually, the vocal cords have a shape which arcuately extends in a fold-like manner, and exhibit a color which has an approximately white chromaticity. Namely, the vocal cords have a characteristic shape value and chromaticity. When a search process is applied to the in vivo image R based on the shape value and chromaticity of the vocal cords, therefore, the glottis G1 contained in the in vivo image R can be surely detected.

In addition to the feature amount of the glottis G2, preferably, the feature amount storing section 12 may store feature amounts of peripheral sites of the glottis G2, such as the epiglottis and the arytenoid cartilage. This enables the detecting section 10 to apply a search process to the in vivo image R based on the feature amounts of the glottis G2 and peripheral sites of the glottis G2 which are stored in the feature amount storing section 12, and to accurately detect the glottis G1 contained in the in vivo image R, based on the degree of similarity with the glottis G2 and the degree of association with the peripheral sites of the glottis G2.

The feature amount storing section 12 may further store: the feature amount of the glottis G2 which is acquired in real time from the subject S who is under measurement by the intubation apparatus; feature amounts of the glottis G2 which are acquired in past measurements; feature amounts of the glottis G2 which are acquired in past measurement from another subject; or feature amounts which are calculated by collecting these glottises G2, and which are then calculated. The feature amount of the glottis G2 is not limited to that which is measured by the intubation apparatus, and data which are collected by an external medical apparatus or the like may be used as the feature amounts.

Preferably, the feature amount storing section 12 may store the feature amounts of the glottis G2 which have various forms. For example, the feature amounts of the glottis G2 which is deformed due to a disease, those of the glottis G2 to which a shielding material such as the blood or vomitus is attached, or the like may be stored. Even in the case where the glottis G1 contained in the in vivo image R has a rare shape, therefore, the detecting section 10 can surely detect the glottis G1.

The result of the detection of the glottis G1 is supplied from the detecting section 10 to the notification controller 11.

Figure 5:
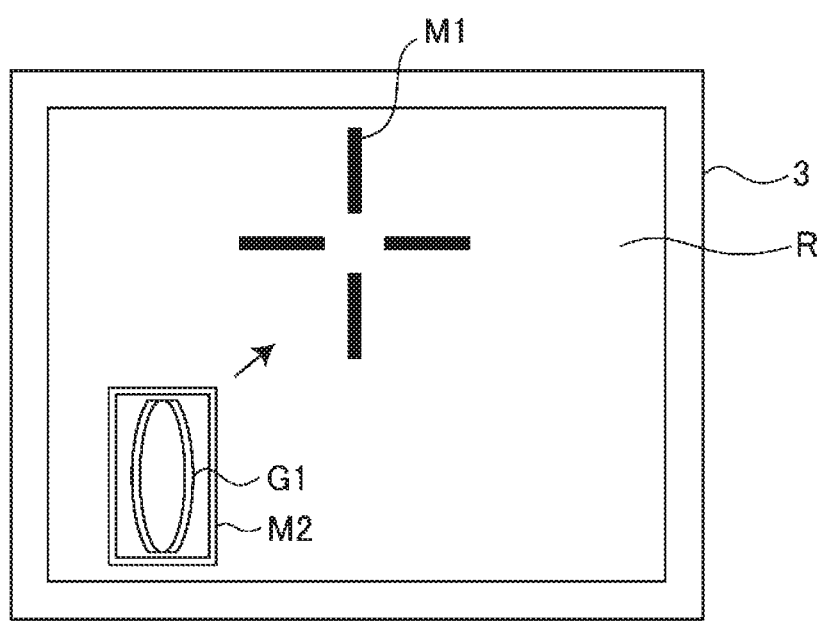
FIG. 5 is a view illustrating a manner of displaying a site mark while being superimposed on the in vivo image.

When the result of the detection of the detecting section 10 is supplied to the notification controller 11, the notification controller 11 changes the display state of the displaying section 3 through the display controller 9 based on the detection result, thereby notifying of the supporting information for supporting an operation of the inserting section 2. In the case where the glottis G1 is detected by the detecting section 10, for example, the notification controller 11 causes the site mark M2 to be displayed on the displaying section 3 at the position of the glottis G1 which is detected by the detecting section 10, with superimposed on the in vivo image R as illustrated in FIG. 5. This enables the operator to quickly know the position of the glottis G1 in the in vivo image R, i.e., to guide the operation of the inserting section 2 so as to coincide with the advancing direction of the intubation tube 4. The site mark M2 may be displayed in yellow.

If the position of the glottis G1 coincides with that of the target mark M1 in this way, and the operator determines that the intubation tube 4 can be inserted into the glottis G1, the intubation tube 4 is caused to forward advance, and the tip end portion of the intubation tube 4 is inserted into the glottis G1. At this time, the operator adjusts the insertion distance of the intubation tube 4 with using the insertion mark 4a which is disposed on the side surface of the intubation tube 4, as an index, and therefore the intubation tube 4 can be easily inserted to an adequate position.

According to the embodiment, the detecting section 10 detects the glottis G1 from the in vivo image R which is taken by the imaging section 5, based on the feature amount of the glottis G2 that is preset, and, when the detecting section 10 detects the glottis G1, the notification controller 11 causes the site mark M2 to be displayed at the position of the glottis G1. Therefore, the operation of the inserting section 2 can be guided, and the intubation tube 4 can be quickly inserted into the glottis G1.

Embodiment 2

Although, in above-described Embodiment 1, the notification controller 11 causes the site mark M2 to be displayed at the position of the glottis G1 which is detected by the detecting section 10, thereby notifying of the supporting information for supporting the operation of the inserting section, the presently disclosed subject matter is limited to the configuration where the site mark M2 is displayed, as far as the supporting information can be notified by changing the display state of the displaying section 3 based on the detection result of the detecting section 10.

Figure 6:
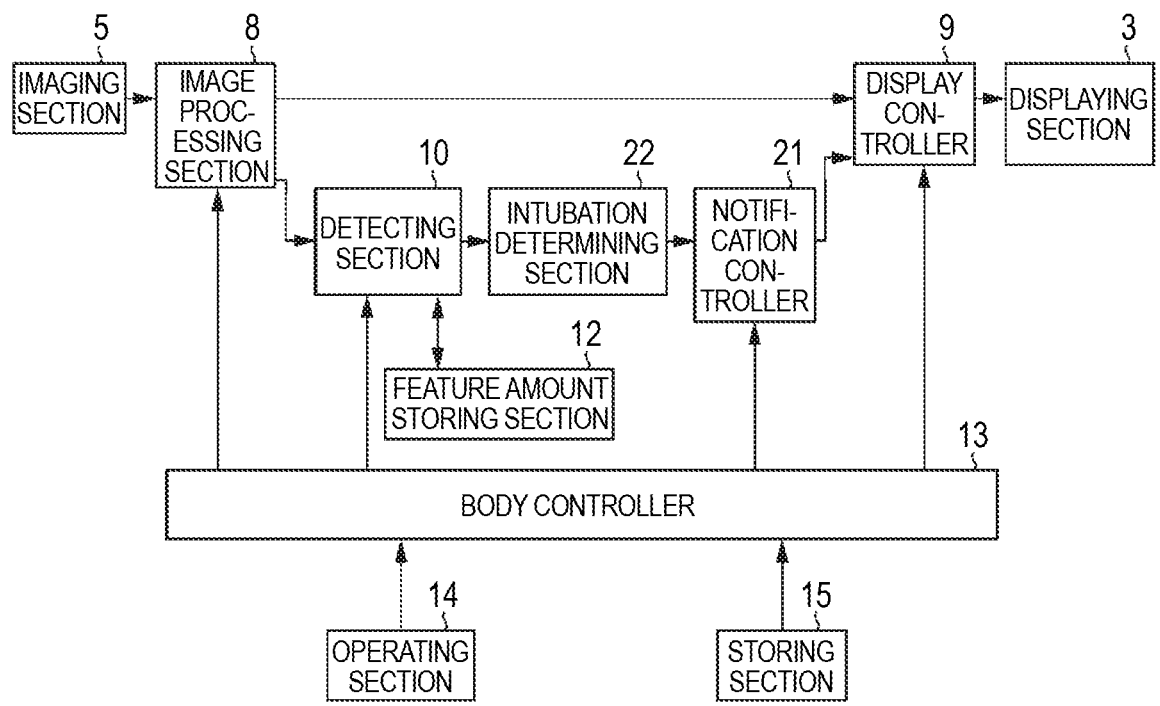
FIG. 6 is a block diagram illustrating the configuration of an apparatus body in Embodiment 2.

As illustrated in FIG. 6, for example, a notification controller 21 may be placed in place of the notification controller 11 in Embodiment 1, and an intubation determining section 22 may be newly placed between the detecting section 10 and the notification controller 21.

The intubation determining section 22 determines whether the intubation tube 4 can be inserted into the glottis G1 or not, based on the position of the glottis G1 which is detected by the detecting section 10, and the advancing direction of the intubation tube 4. Namely, the intubation determining section 22 determines whether the position of the glottis G1 which is detected by the detecting section 10 exists in the advancing direction of the intubation tube 4 or not. Here, the advancing direction of the intubation tube 4 can be set based on, for example, the forming direction of the groove portion 7 in the inserting section 2.

The notification controller 21 changes the display state of the displaying section 3 through the display controller 9 based on the result of the determination of the intubation determining section 22, thereby notifying of supporting information for supporting an operation of the inserting section 2 by the operator. If the intubation determining section 22 determines that the intubation tube 4 can be inserted into the glottis G1, specifically, the notification controller 21 changes the display state of the site mark M2 which is displayed while being superimposed on the in vivo image R, thereby notifying of the supporting information.

According to the configuration, in the same or similar manner as Embodiment 1, the detecting section 10 detects the glottis G1 contained in the in vivo image R based on the feature amount of the glottis G2. When the position of the detected glottis G1 is supplied from the detecting section 10 to the intubation determining section 22, the intubation determining section 22 determines whether the intubation tube 4 can be inserted into the glottis G1 or not, based on the position of the glottis G1, and the advancing direction of the intubation tube 4, i.e. the position of the target mark M1.

Figure 7:
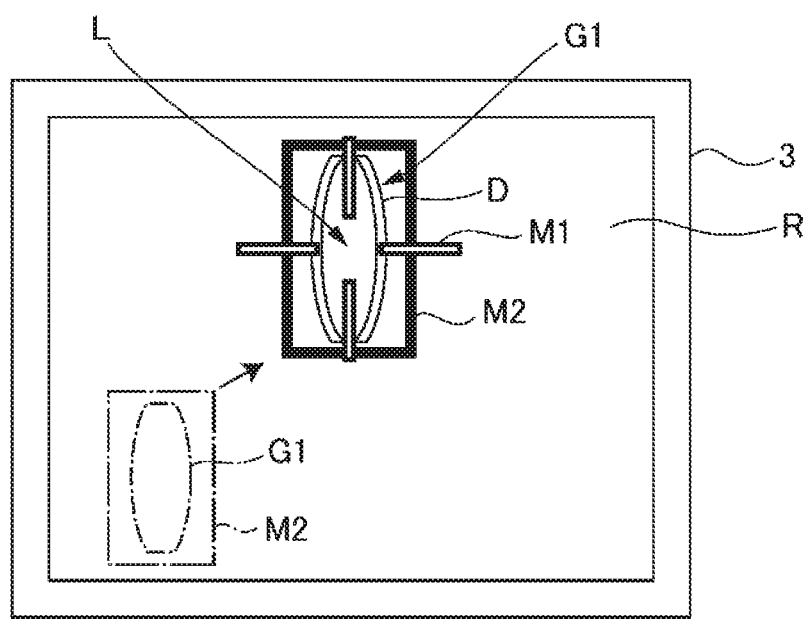
FIG. 7 is a view illustrating a manner of operating an inserting section so that an image of the glottis overlaps with the target mark.

If the position of the glottis G1 is different from that of the target mark M1 as illustrated in FIG. 5, for example, the intubation determining section 22 determines that the intubation tube 4 cannot be inserted into the glottis G1. If the position of the glottis G1 coincides with that of the target mark M1, by contrast, the intubation determining section 22 determines that the intubation tube 4 can be inserted into the glottis G1. In the case where the operator operates the inserting section 2 so that the image of the glottis G1 overlaps with the target mark M1 as illustrated in FIG. 7, for example, the position of the glottis G1 which is detected by the detecting section 10 coincides with that of the target mark M1, and the intubation determining section 22 determines that the intubation tube 4 can be inserted into the glottis G1.

The intubation determining section 22 supplies the result of the determination to the notification controller 21.

When the result of the determination of the intubation determining section 22 is supplied to the notification controller 21, the notification controller 21 changes the display state of the displaying section 3 through the display controller 9, in accordance with the determination result of the intubation determining section 22, thereby notifying of supporting information for supporting an operation of the inserting section 2 by the operator.

If the intubation determining section 22 determines that the intubation tube 4 cannot be inserted into the glottis G1, specifically, the notification controller 21 causes the yellow site mark M2 at the position of the glottis G1 which is detected by the detecting section 10, in the same or similar manner as Embodiment 1. If the intubation determining section 22 determines that the intubation tube 4 can be inserted into the glottis G1, by contrast, the notification controller 21 changes the color of the site mark M2 to a color which is different from yellow.

When the color of the yellow site mark M2 is changed as described above, an operation of the inserting section 2 can be guided so that the position of the glottis G1 coincides with the advancing direction of the intubation tube 4, and the operator can easily know that the intubation tube 4 can be inserted into the glottis G1.

For example, the color of the site mark M2 may be changed from yellow to green.

Here, preferably, the target mark M1 may have a shape which indicates the outer diameter of the intubation tube 4. As illustrated in FIG. 7, for example, the target mark M1 may have, in a middle portion, a shape which forms a gap L according to the outer diameter of the intubation tube 4. According to the configuration, the size of the image of the glottis G1, for example, the distance between the vocal cords D with respect to the gap L changes in accordance with the insertion distance by which the inserting section 2 is inserted into the body, and therefore supporting information for supporting the operation of the inserting section 2 by the operator can be notified.

In the case where the distance between the vocal cords D is small with respect to the gap L of the target mark M1, specifically, it is determined that the insertion distance of the inserting section 2 is short, namely, a tip end portion of the inserting section 2 is located remotely from the glottis G1, and the inserting section 2 is further advanced toward the glottis G1. In order to more accurately adjust the insertion position of the inserting section 2, preferably, the degree of the insertion distance is determined by determining not only the distance but also the size of the glottis G1. According to the configuration, the operator can easily know that the inserting section 2 is inserted to a predetermined insertion position in the body of the subject, namely, the tip end portion of the intubation tube 4 is located at an adequate distance from the glottis G1, and therefore the inserting section 2 can be guided to the predetermined insertion position.

As described above, if it is determined that the intubation tube 4 can be inserted into the glottis G1, the operator forwardly advances the intubation tube 4, and inserts the tip end portion of the intubation tube 4 into the glottis G1.

According to the embodiment, the intubation determining section 22 determines whether the intubation tube 4 can be inserted into the glottis G1 or not, and the notification controller 21 changes the display state of the displaying section 3 based on the result of the determination of the intubation determining section 22, thereby notifying of supporting information. Therefore, an operation of the inserting section 2 can be guided so that the position of the glottis G1 coincides with the advancing direction of the intubation tube 4, and the intubation tube 4 can be quickly inserted into the glottis G1.

Embodiment 3

In Embodiments 1 and 2 which are described above, the detecting section 10 can detect also a non-target site which is different from the glottis G1.

Figure 8:
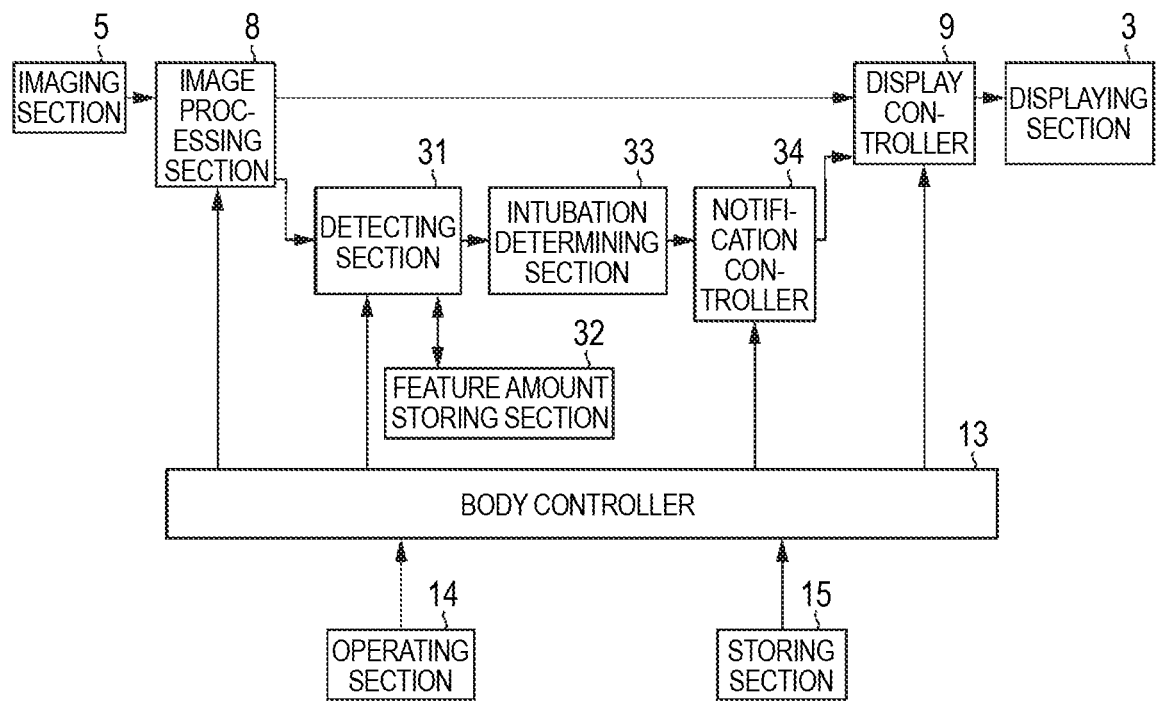
FIG. 8 is a block diagram illustrating the configuration of an apparatus body in Embodiment 3.

As illustrated in FIG. 8, for example, a detecting section 31, a feature amount storing section 32, an intubation determining section 33, and a notification controller 34 may be placed respectively in place of the detecting section 10, feature amount storing section 12, intubation determining section 22, and notification controller 21 in Embodiment 2.

The feature amount storing section 32 stores the feature amount of the glottis G2, and also that of a non-target site which is different from the glottis G1, such as the esophagus. Examples of the feature amount of the esophagus are the shape value of the esophagus, the chromaticity of the esophagus, and the like.

The detecting section 31 detects the glottis G1 from the in vivo image R which is taken by the imaging section 5, as the target site based on the feature amount of the glottis G2 which is read from the feature amount storing section 32. The detecting section 31 further detects the esophagus from the in vivo image R which is taken by the imaging section 5, as a non-target site based on the feature amount of the esophagus which is read from the feature amount storing section 32.

The intubation determining section 33 determines whether the intubation tube 4 can be inserted into the glottis G1 or not, based on the position of the glottis G1 which is detected by the detecting section 31, and the advancing direction of the intubation tube 4. The intubation determining section 33 further determines whether the intubation tube 4 can be inserted into the esophagus or not, based on the position of the esophagus which is detected by the detecting section 31, and the advancing direction of the intubation tube 4.

In the case where the detecting section 31 detects the esophagus, the notification controller 34 changes the display state of the displaying section 3, thereby notifying of supporting information for supporting an operation of the inserting section 2 by the operator. In the case where the intubation determining section 33 determines that the intubation tube 4 can be inserted into the glottis G1, the notification controller 34 further changes the display state of the displaying section 3, thereby notifying of supporting information. In the case where the intubation determining section 33 determines that the intubation tube 4 can be inserted into the esophagus, the notification controller 34 further changes the display state of the displaying section 3, thereby notifying of supporting information.

Figure 9:
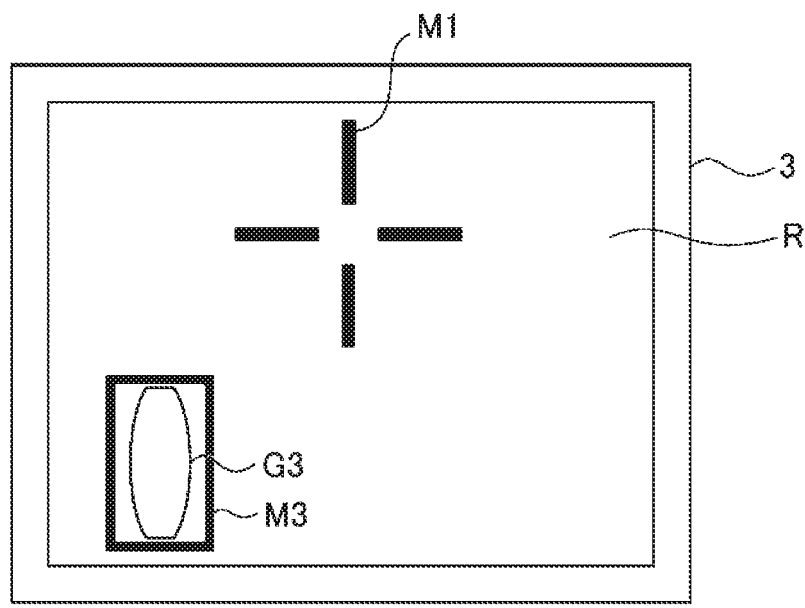
FIG. 9 is a view illustrating a manner of detecting the esophagus contained in the in vivo image.

According to the configuration, when the detecting section 31 detects the esophagus contained in the in vivo image R based on the feature amount of the esophagus, the notification controller 34 causes a non-site mark which is different from the site mark M2, at the position of the esophagus while being superimposed on the in vivo image R. As illustrated in FIG. 9, when the detecting section 31 detects the esophagus G3 contained in the in vivo image R, for example, the notification controller 34 causes a non-site mark M3 of a color which is different from that of the site mark M2, at the position of the esophagus G3, while being superimposed on the in vivo image R. When the non-site mark M3 is displayed while its color is made different from the color of the site mark M2 in this way, the operator can easily recognize the existence of the esophagus G3 which is a non-target site, and the operation of the inserting section 2 can be guided so that the glottis G1 is displayed on the displaying section 3.

For example, the non-site mark M3 may be displayed in red.

When the inserting section 2 is operated so that the image of the esophagus G3 overlaps with the target mark M1, the position of the esophagus G3 which is detected by the detecting section 31 is made coincident with that of the target mark M1. Therefore, the intubation determining section 33 determines that the intubation tube 4 can be inserted into the esophagus G3.

If the intubation determining section 33 determines that the intubation tube 4 can be inserted into the esophagus G3, the notification controller 34 changes the display state of the displaying section 3, thereby notifying the operator of an erroneous operation of the inserting section 2.

Figure 10:
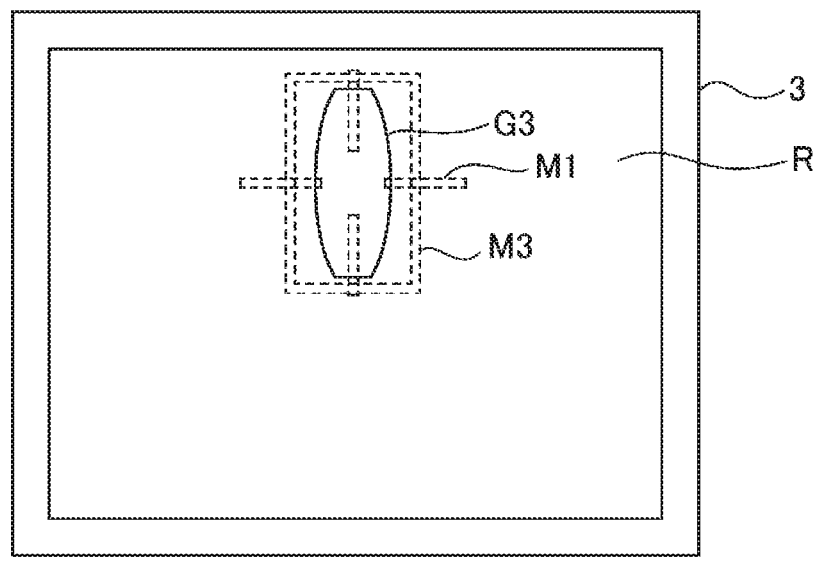
FIG. 10 is a view illustrating a manner of operating the inserting section so that an image of the esophagus overlaps with the target mark.

As illustrated in FIG. 10, for example, the notification controller 34 erases the target mark M1 and non-site mark M3 which are displayed with superimposed on the in vivo image R, thereby notifying the operator of the erroneous operation of the inserting section 2. When the target mark M1 and the non-site mark M3 are erased as described above, the operator can surely notice the erroneous operation of the inserting section 2, and intubation into the esophagus G3 can be prevented from occurring.

Here, the operator performs the operation while gazing the in vivo image R displayed on the displaying section 3, and there is therefore a possibility that, even when the erroneous operation of the inserting section 2 is notified by a warning sound or the like, the operator fails to notice the erroneous operation. When the notification controller 34 changes the display state of the displaying section 3, therefore, the erroneous operation of the inserting section 2 can be surely notified to the operator. Alternatively, the notification controller 34 may erase only the target mark M1, thereby notifying the operator of the erroneous operation of the inserting section 2.

When the operator recognizes the erroneous operation of the inserting section 2 as described above, the position of the glottis G1 is again searched, and, in the same or similar manner as Embodiment 1, the intubation tube 4 is inserted into the glottis G1.

According to the embodiment, the detecting section 31 detects the esophagus G3 from the in vivo image which is taken by the imaging section 5, based on the feature amount of the esophagus G3 which is preset, and the notification controller 34 changes the display state of the displaying section 3 based on the detection result of the detecting section 31, whereby the operation of the inserting section 2 can be guided so that the glottis G1 is displayed on the displaying section 3, and therefore the intubation tube 4 can be quickly inserted into the glottis G1.

Embodiment 4

Although, in above-described Embodiments 1 to 3, the supporting information for supporting an operation of the inserting section 2 is notified by changing the display state of the displaying section 3, the notifying section is not limited to use the displaying section 3 as far as the notifying section can perform the notification.

Figure 11:
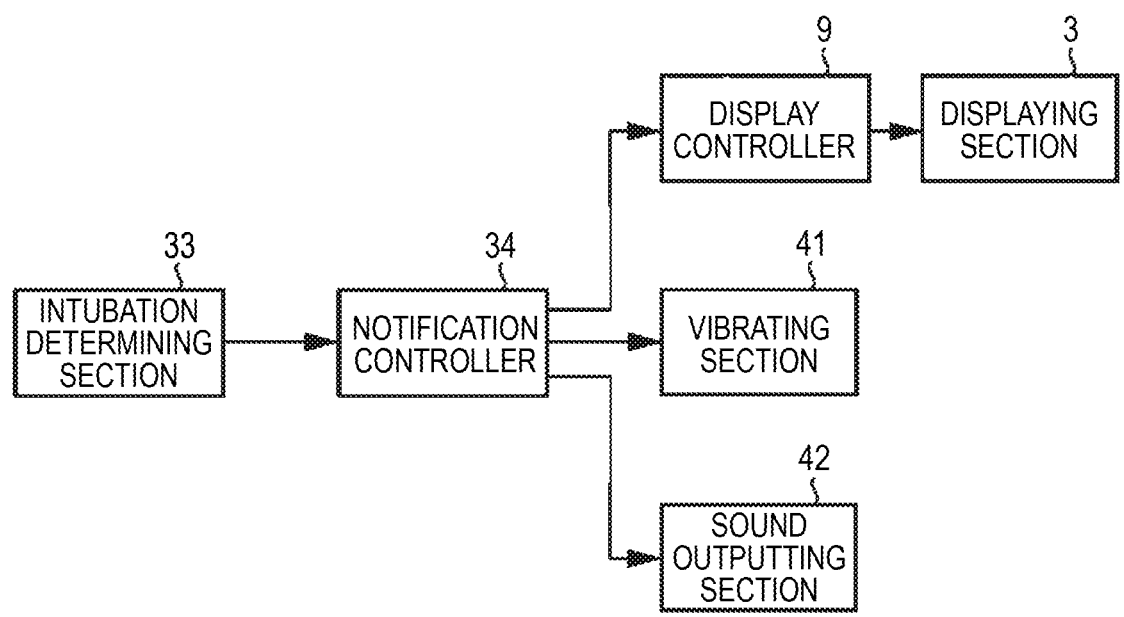
FIG. 11 is a block diagram illustrating the configurations of main sections of an apparatus body in Embodiment 4.

As illustrated in FIG. 11, in Embodiment 3, for example, a vibrating section 41 and a sound outputting section 42 may be newly placed, and the vibrating section 41 and the sound outputting section 42 may be connected to the notification controller 34.

The vibrating section 41 vibrates the grasping portion 6 in the apparatus body 1 to notify the operator of the erroneous operation of the inserting section 2. For example, the vibrating section 41 may be configured by a vibrator.

The sound outputting section 42 outputs a warning sound in the apparatus body 1 to notify the operator of the erroneous operation of the inserting section 2. For example, the sound outputting section 42 may be configured by a speaker. The sound outputting section 42 may be placed in an external apparatus for the intubation apparatus, such as a patient monitor, a defibrillator, or a respirator.

According to the configuration, in the same or similar manner as Embodiment 3, if the intubation determining section 33 determines that the intubation tube 4 can be inserted into the glottis G3, the notification controller 34 changes the display state of the displaying section 3. Moreover, the notification controller 34 causes the vibrating section 41 to vibrate, and the sound outputting section 42 to output a warning sound. As described above, in addition to a change of the display state of the displaying section 3, the vibration and the warning sound are output, and therefore the operator can more surely recognize the erroneous operation of the inserting section 2.

According to the embodiment, if the intubation determining section 33 determines that the intubation tube 4 can be inserted into the esophagus G3, the notification controller 34 causes the vibrating section 4 to vibrate, and the sound outputting section 42 to output the warning sound. Therefore, the erroneous operation can be more surely notified to the operator.

In the embodiment, alternatively, the notifying section may be configured by eliminating the displaying section 3, and by using at least one of the vibrating section 41 and the sound outputting section 42.

Embodiment 5

Although, in above-described Embodiments 1 to 4, the detecting section detects the glottis G1 as the target site, the target site can be arbitrarily selected by the operator, and is not limited to the glottis G1.

Figure 12:
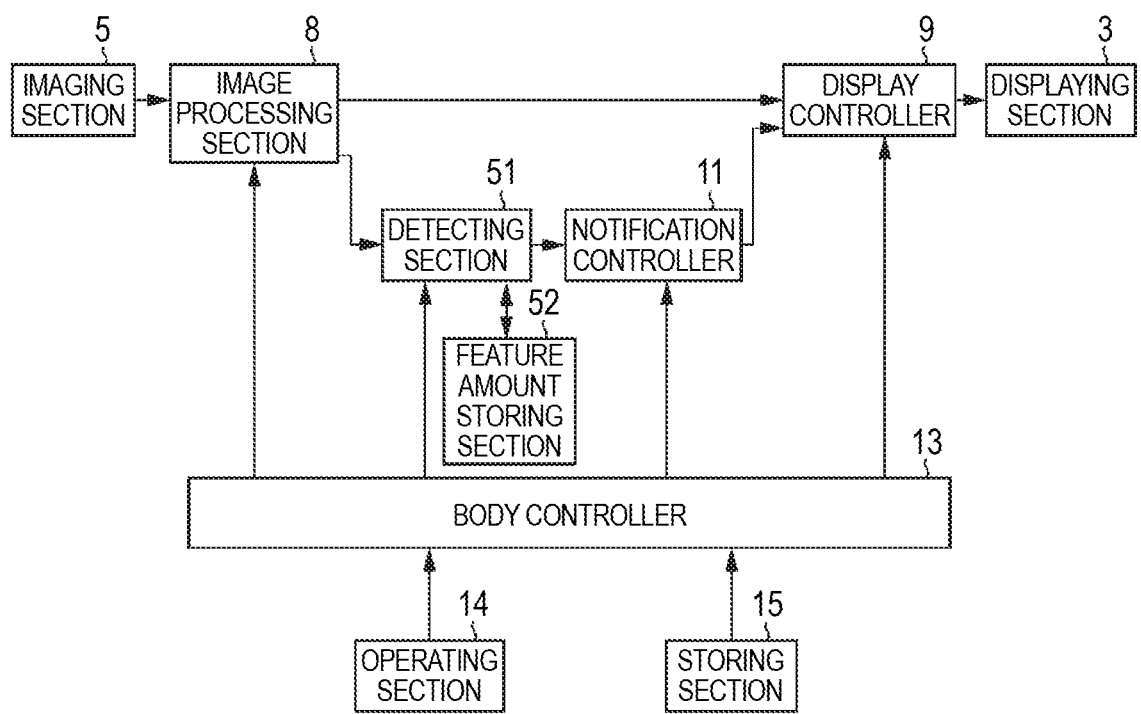
FIG. 12 is a block diagram illustrating the configuration of an apparatus body in Embodiment 5.

As illustrated in FIG. 12, for example, a detecting section 51 may be placed in place of the detecting section 10 in Embodiment 1, and a feature amount storing section 52 may be placed in place of the feature amount storing section 12.

The feature amount storing section 52 stores the feature amount of the glottis G2, and also that of the esophagus G3.

The detecting section 51 is configured so as to switch over between a glottis detection mode and an esophagus detection mode. In the glottis detection mode, the detecting section detects the glottis G1 as the target site, and, in the esophagus detection mode, detects the esophagus as the target site.

According to the configuration, when the operator operates the operating section 14 to set the detecting section 51 to the esophagus detection mode, the detecting section 51 detects the esophagus G3 from the in vivo image R which is taken by the imaging section 5, based on the feature amount of the esophagus G3 which is stored in the feature amount storing section 52. In the case where the esophagus G3 is detected by the detecting section 51, then, the notification controller 11 causes the site mark to be displayed at the position of the esophagus G3. This enables the operator to easily recognize the position of the esophagus G3 in the in vivo image R, and to quickly insert the intubation tube 4 into the esophagus G3.

According to the embodiment, the detecting section 51 is configured so as to be able to switch over between the glottis detection mode in which the glottis G1 is detected as the target site, and the esophagus detection mode in which the esophagus G3 is detected as the target site, and therefore intubation according to the object of the operator can be surely performed.

Although, in above-described Embodiments 1 to 5, the notification controller changes the colors of the target mark M1, the site mark M2, and the non-site mark M3, the presently disclosed subject matter is not limited to this as far as the display state of the displaying section 3 can be changed. For example, the notification controller may change the shapes of the target mark M1, the site mark M2, and the non-site mark M3, or supporting information for supporting an operation of the inserting section 2 may be displayed with characters on the displaying section 3.

Although, in above-described Embodiments 1 to 5, the displaying section 3 is disposed integrally with the apparatus body 1, the displaying section may be placed separately from the apparatus body 1 as far as the in vivo image R which is taken by the imaging section 5 can be displayed on the displaying section.

Although, in above-described Embodiments 1 to 5, the notification controller changes the display state of the displaying section 3 based on the detection result of the detecting section, the means for changing the display state is not limited to the notification controller as far as the display state of the displaying section 3 can be changed. For example, the display controller 9 may change the display state of the displaying section 3 based on the detection result of the detecting section.

Although, in above-described Embodiments 1 to 5, the notification controller controls the notifying section so as to notify of supporting information for supporting an operation of the inserting section 2, the information to be notified is not limited to supporting information as far as information relating to the target site of the subject can be notified. For example, the detecting section may detect information of presence or absence of a tumor, sputum, and burn in the cavity of the mouth of the subject, and the notification controller may control the notifying section so as to notify of observation information indicating the state of the target site of the subject, based on the information detected by the detecting section. This enables the operator to perform adequate treatment in accordance with the state of the target site of the subject.

What is claimed is:

1. An intubation apparatus comprising:
    an inserting section that has an elongated shape and is to be inserted from a mouth of a subject into a body of the subject;
    an intubation tube that is formed to extend along a longitudinal direction of the inserting section and is disposed to be advanceable and retractable with respect to the inserting section;
    an imaging section that is placed in a vicinity of a tip end portion of the inserting section and is configured to take an in vivo image of the body of the subject;
    a detecting section that is configured to detect a glottis as a target site in the in vivo image taken by the imaging section, based on comparing data in the in vivo image to predetermined shape information of the target site;
    a display that is disposed integrally with or separately from the insert inserting section and is configured to notify an operator who operates the inserting section, of information; and
    a notification controller that is configured to control the display to display the in vivo image with information indicative of a position of the target site of the subject superimposed thereon, based on a result of the detection by the detecting section.

2. The intubation apparatus according to claim 1, wherein the notification controller is configured to change a display state of the display to display supporting information for supporting an operation of the inserting section, based on the result of the detection of the detecting section.

3. The intubation apparatus according to claim 2, further comprising an intubation determining section configured to determine whether an intubation tube is insertable into the target site or not, based on a position of the target site which is detected by the detecting section and a direction for advancing of the intubation tube toward the target site,
    wherein the notification controller is configured to change a display state of the display based on the result of the determination of the intubation determining section to display the supporting information.

4. The intubation apparatus according to claim 3, wherein when the intubation determining section determines that the intubation tube is insertable into the target site, the notification controller is configured to change a display state of the site mark which is displayed at the position of the target site that is detected by the detecting section while being superimposed on the in vivo image to display the supporting information.

5. The intubation apparatus according to claim 3, wherein the detecting section is configured to detect the non-target site which is different from the target site, from the in vivo image based on shape information of the non-target site,
    the intubation determining section is configured to determine whether the intubation tube is insertable into the non-target site or not, based on a position of the non-target site which is detected by the detecting section, and the direction for advancing of the intubation tube, and
    when the intubation determining section determines that the intubation tube is insertable into the non-target site, the notification controller is configured to erase a target mark which is displayed on the display.

6. The intubation apparatus according to claim 5, further comprising at least one of a vibrating section configured to vibrate a grasping portion that is to be grasped by an operator, and a sound outputting section configured to output a warning sound to the operator, and
    when the intubation determining section determines that the intubation tube is insertable into the non-target site, the notification controller is configured to cause at least one of the vibrating section and the sound outputting section to operate.

7. The intubation apparatus according to claim 2, wherein the display is configured to display the target mark indicating a direction for advancing the intubation tube toward the target site, while being superimposed on the in vivo image,
    the target mark having a shape which indicates an outer diameter of the intubation tube, and a size of the target site with respect to the shape is changed in accordance with an insertion distance by which the inserting section is inserted into a body.

8. The intubation apparatus according to claim 1, wherein when the target site is detected by the detecting section, the notification controller is configured to cause a site mark to be displayed at a position of the target site while the site mark is superimposed on the in vivo image.

9. The intubation apparatus according to claim 8, wherein based on shape information of a non-target site which is different from the target site, the detecting section is configured to detect the non-target site from the in vivo image, and,
    in a case where the non-target site is detected by the detecting section, the notification controller is configured to cause a non-site mark which is different from the site mark, to be displayed at a position of the non-target site while being superimposed on the in vivo image.

10. The intubation apparatus according to claim 1, wherein the information indicative of the position of the target site overlaps the target site.

11. The intubation apparatus according to claim 1, wherein the detecting section is configured to detect shape information of the vocal chords.

12. The intubation apparatus according to claim 1, wherein the display is configured to display a target mark indicating a direction for advancing the intubation tube toward the target site, while the target mark is superimposed on the in vivo image.

13. The intubation apparatus according to claim 1, wherein the intubation tube has an insertion mark at a tip end portion thereof, the insertion mark functioning as a guide when inserting the insertion tube into the glottis.

* * * * *

UNITED STATES PATENT AND TRADEMARK OFFICE
CERTIFICATE OF CORRECTION

PATENT NO. : 11,511,064 B2
APPLICATION NO. : 16/365911
DATED : November 29, 2022
INVENTOR(S) : Yukio Taniguichi It is certified that error appears in the above-identified patent and that said Letters Patent is hereby corrected as shown below:

In the Claims

Column 13, Line 33, Claim 1 "from the insert inserting section" should read -- from the inserting section --

Signed and Sealed this
Twenty-sixth Day of December, 2023

Katherine Kelly Vidal
*Director of the United States Patent and Trademark Office*